United States Patent [19]

Welle et al.

[11] 4,060,631
[45] Nov. 29, 1977

[54] AMINOETHYL OXIME ETHERS HAVING ANTI-DEPRESSIVE ACTIVITY

[75] Inventors: Hendricus Bernardus Antonius Welle, Utrecht; Volkert Claassen, Weesp, both of Netherlands

[73] Assignee: U.S. Philips Corporation, New York, N.Y.

[21] Appl. No.: 668,491

[22] Filed: Mar. 19, 1976

[30] Foreign Application Priority Data

Mar. 20, 1975 Netherlands .......................... 7503308

[51] Int. Cl.² .................. A61K 31/15; A61K 31/275; C07C 131/00
[52] U.S. Cl. .............................. 424/304; 260/465 E; 260/501.17; 260/566 AE; 424/316; 424/327; C07C/121/80
[58] Field of Search ................. 260/566 AE; 424/327, 424/465 F, 501.17, 304, 316

[56] References Cited

U.S. PATENT DOCUMENTS 3,692,835  9/1972  Van Dijk et al. ............. 260/566 AE Primary Examiner—Dolph H. Torrence
Attorney, Agent, or Firm—Frank R. Trifari; Norman N. Spain

[57] ABSTRACT

Compounds of the formula

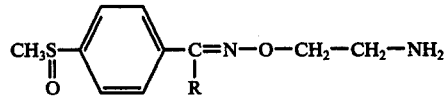

wherein R is alkyl of 4 to 6 carbons, benzyl, 4-ethoxybutyl, 5 ethoxypentyl, 4-cyanobutyl or 5-cyanopentyl exhibit strong serotonine potentiation with no monoamino oxidase inhibition and are substantially free of side effects.

12 Claims, No Drawings

AMINOETHYL OXIME ETHERS HAVING ANTI-DEPRESSIVE ACTIVITY

The invention relates to the novel oxime ether compounds having anti-depressive activity.

British patent specification No. 1,205,655 describes a large group of compounds as having an anti-depressive, a sedative and/or an anti-convulsive activity. According to said Patent Specification the anti-depressive activity of the known compounds is based on monoamino oxidase (MAO) inhibition and/or on noradreline potentiation.

Compounds which inhibit MAO are particularly difficult to administer. They often have serious side effects and often are imcompatible with other medicines and with nutrients. As the regulations which govern the use of medicines becomes more and more stringent, only certain compounds which are substantially free from noxious side effects can be considered for administration to human beings.

It is the object of the invention to provide novel anti-depressive compounds which do not have an activity component based on MAO inhibition and which are substantially free from noxious side effects and whose activity is primarily expressed in an elevation of mood of the treated patient and to a much smaller extent in an increase of the motor activity.

Biochemical investigations in depressive patients (Brit. J. Psychiatr. 113 1407 (1967), Nature 225 1259 (1970) and Arch Gen. Psychiatr. 28 827 (1973) have lent support to the hypothesis that a decrease of the serotonergic processes in the brains is a factor in the pathogenesis of depressions.

However, investigations in other patients do not lead to this supposition (Arch. Gen. Psychiatr. 25 354 (1971). Therefore, a current opinion, which is gaining support, is that there are various "sub-type" classifications of patients whose depressions are caused by different deviations in the metabolism of biogenic amines. This can explain why patients who fall into these different sub-type classifications of depression react differently to the treatment with anti-depressive compounds (Drugs 4 361 (1972)).

The anti-depressive compounds now clinically used influence to a different extent the re-uptake of amines in the neurons : desmethylimipramine and protriptyline have mainly a blocking effect on the cell membrane of noradrenergic neurons, while imipramine and amitriptyline in addition inhibit the re-uptake of serotonine by serotonergic neurons (j. Pharm. Pharmacol. 20 150 (1968), J. Paramacol. 4 135 (1968)).

There are a number of brain processes in which serotonine and noradrenaline have opposite activities (Ann. N.Y. Acad. Sci. 66 631 (1957), Adv. Pharmacol. 6B 97 (1968) and Jouvet in Van Praag: Brain and Sleep 1974). In the medicinal treatment of depressive patients, the intensification of the function of one amine might result in a decrease of the function of the other amine.

As a means to elevate the mood of depressive patients there exists, on the basic of the above, a significant need in pharmacy for a compound whose activity consists mainly of a blocking of the cell membrane of the serotonergic neurons (Van Praag, Psyche aan banden, De Erven Bohn B.V. Amsterdam, 1974), i.e. whose activity is mainly based on the potentiation of serotonine.

It was found that the novel compounds of formula I

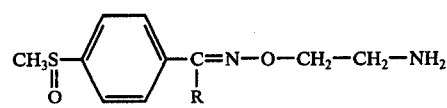

and salts thereof with pharmaceutically acceptable acids fulfil the imposed requirements. The compounds give a very powerful serotonine potentiation which is associated with a weaker noradrenaline potentiation. The compounds do not have an activity component based on monoamino oxidase inhibition, are substantially free from side effects, for example stomach ulceration and broncho-constriction, and have a very low toxicity.

In formula I, R has the following meaning: a linear alkyl group having 4–6 C atoms, a benzyl group, a 4-ethoxybutyl group, a 5-methoxypentyl group, a 4-cyano butyl group or a 5-cyanopentyl group.

While it is surprising that a very strong serotonine potentiation was found for the novel compounds when compared with the compounds known from British patent specification No. 1,205,665 which known compounds only have an antidepressive activity based on noradrenaline potentiation and/or on MAO inhibition even more surprising is the selectivity by which the compounds according to the invention potentiate serotonine (expressed in the low ratios $ED_{50}$ serotonine potentiation /$ED_{50}$ noradrenaline potentiation (serot.-/noradr.)).

As there are no compounds with a methylsulfinyl group described in the said British patent specification No., the compounds according to the invention were compared with two methylthio-substituted compounds, namely the closest structurally related compounds from British patent specification. The results of this investigation are recorded in the following table.

| $S_1$ | Compound S | | noradr. pot. | serot. pot. | serot./noradr. | MAO inhib. | Stomach ulcer. | broncho constr. |
|---|---|---|---|---|---|---|---|---|
| $CH_3SO$ | $(CH_2)_3CH_3$ | * | 60 | 15 | 0.25 | >215 | — | — |
| $CH_3SO$ | $(CH_2)_4CH_3$ | ** | 42 | 27 | 0.6 | >215 | — | — |
| $CH_3SO$ | $(CH_2)_5CH_3$ | * | 147 | 32 | 0.2 | >215 | — | — |
| $CH_3SO$ | $CH_2C_6H_5$ | ** | 38 | 29 | 0.8 | >215 | — | — |
| $CH_3SO$ | $(CH_2)_4OC_2H_5$ | * | 73 | 15 | 0.2 | >215 | — | — |
| $CH_3SO$ | $(CH_2)_5OCH_3$ | | 33 | 28 | 0.8 | >215 | — | — |
| $CH_3SO$ | $(CH_2)_4CN$ | * | >100 | 44 | <0.4 | >215 | — | — |
| $CH_3SO$ | $(CH_2)_5CN$ | | 100 | 35 | 0.4 | >215 | — | — |
| $CH_3S$ | $CH_3$ | ** | 2.4 | 0.74 | 0.3 | 15 | — | — |

-continued

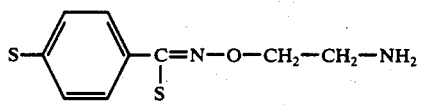

| $S_1$ | Compound S | noradr. pot. | serot. pot. | serot./ noradr. | MAO inhib. | Stomach ulcer. | broncho constr. |
|---|---|---|---|---|---|---|---|
| CH₃S | (CH₂)₄CH₃ | ** | ~50 | 10 | ~0.2 | >215 | + | + |

\* = fumarate 1:1
\*\* = hydrochloride.

In this table the ratios ED₅₀ denote values expressed in mg/kg. In the column serot./noradr. the ratio of the ED₅₀ values are recorded from the two preceding columns.

The selectivity of the compounds with respect to serotonine potentiation and furthermore the absence of undesired effects such as MAO inhibition, stomach ulceration and broncho-constriction appear clearly from this table.

Although the first of the known compounds recorded below the dividing line also has a powerful and a selective serotonine potentiation, this known substance does not satisfy the object of the invention, since the substance also inhibits monoamino-oxidase to a very considerable extent. The second known compound does not meet the above-mentioned requirements because the compound causes both stomach ulceration and broncho-constriction.

In addition to the surprisingly powerful and selective serotonine potentiation, the absence of the said undesired side effects in the compounds according to the invention is very unexpected since these side effects are present indeed in known structurally related compounds.

The results recorded in the table were obtained in the following tests.

The noradrenaline potentiation was determined in the tetrabenazine test. In this test a quantity of the compound to be tested were administered orally to five male albino mice. After 45 minutes the animals were injected subcutaneously with 80 mg/kg of tetrabenazine. After another 45 minutes the degree of ptosis was determined and compared with the ptosis of animals which had received tetrabenazine alone. The ED₅₀ was determined from the results.

The serotonine potentiation was determined in the 5-hydroxytryptophan test. For this purpose, the compounds to be tested were administered orally to isolated male albino mice in a series of dosages (five mice per dosage) 1 hour prior to intraperitoneal administration of 150 mg/kg of dl-5-hydroxytryptophan. Thirty minutes after this threshold dosage the mice were observed individually and the following parameters were scored: stereotypical shaking of the head, spreading of the hindlegs, tremor, tendency to flee, lordosis, clonic stamping with the frontlegs. The ED₅₀ value was calculated from the results.

The monoamino-oxidase (MAO) inhibiting effect was determined in experiments in which a quantity of the compound to be tested was administered orally to five male albino mice. One hour later the animals were injected subcutaneously with tryptamine hydrochloride in a quantity of 250 mg/kg. This quantity does not cause mortality in animals which do not receive the compound to be tested, but does cause mortality in animals to which an active substance has been administered. Eighteen hours after the administration of triptamine hydrochloride it was determined how many animals had died. The ED₅₀ was determined from the results.

By means of the method by Metysŏvâ, Arzneimittelforschung 13 1039 (1963), it was determined whether the oral administration of 200 mg of a compound under test causes stomach ulceration.

By means of the method by Konzett-Rössler, Arch. Exp. Path. Pharmakol. 195 71 (1940) it was investigated whether a compound under test causes broncho-constriction after the intravenous administration of 3 mg of the compound. In this method reduction of the breathing function as a result of broncho-constriction is expressed by a smaller volume of air being taken in.

On the basis of their properties the compounds of formula I and their salts are particularly suitable for use in the treatment of depressive patients, in particular for elevation of mood.

The quantity, the frequency and the route by which the substances are administered may vary for each individual patient, and also in accordance with the nature and the severity of the disturbance to be treated. In general, adults will receive a daily dose of from 25–500 mg orally. As a rule, a quantity of from 50 to 200 mg orally daily will be sufficient.

The compounds are preferably used in the form of pills, tablets, coated tablets, capsules, powders, injection liquids and the like. The compounds may be processed to such compositions according to methods which are known per se.

The invention therefore also relates to compositions having a compound of formula I or a salt thereof as an active constituent with a pharmaceutically acceptable acid and to methods to prepare said compositions, for example, by mixing the active substance with or dissolving it in solid or liquid pharmaceutical carrier materials.

As examples of pharmaceutically acceptable acids with which compounds of formula I can form salts may be mentioned: inorganic acids, for example hydrochloric acid, sulphuric acid, nitric acid and organic acids, for example, citric acid, fumaric acid, tartaric acid, benzoic acid, maleic acid and the like.

The compounds of formula I and their salts may be prepared according to methods which are known for the preparation of this type of compounds and according to methods analogous thereto.

The invention also relates to the preparation of the compounds.

They can be obtained inter alia by converting a compound of formula II

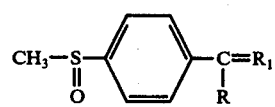

with the compound of formula III H$_2$N—O—CH$_2$—CH$_2$—NH$_2$ or a salt thereof.

In formula II, R has the same meaning as in formula I and R$_1$ is an oxygen atom, an oxime group or an alkylene dioxy group, for example ethylene dioxy. The reaction is preferably carried out in an inert solvent, for example an alcohol, dioxan, dimethyl formamide, tetrahydrofuran or a mixture thereof, at temperatures between room temperature and the boiling point of the mixture, and optionally in the presence of an acid binder, for example pyridine.

Another method consists of a reaction between a compound of formula IV

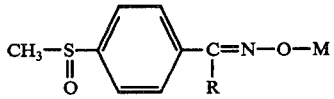

wherein M is a hydrogen atom or an alkali metal atom and R has the same meaning as in formula I and a compound of formula V Hal—CH$_2$—CH$_2$—NH$_2$ or a salt thereof wherein Hal is a halogen atom, preferably a chlorine atom or a bromine atom.

The reaction is preferably carried out in an inert solvent, for example alcohols, ethers or dimethyl formamide. When M is a hydrogen atom, an acid binder, for example an alcoholate, is preferably added. As a rule the reaction temperature is between 0° and 50° C.

The compounds can also be obtained by reacting a compound of formula VI

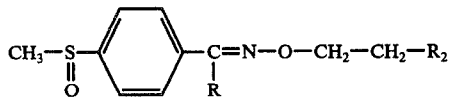

wherein R has the same meaning as in formula I and R$_2$ is a mesyloxy group or a tosyloxy group, with ammonia. The reaction is preferably carried out in an inert solvent, for example an alcohol, usually at temperatures between room temperature and 150° C.

The compound of formula VI can be prepared by converting a compound of formula IV with ethylene oxide in ethanol and in the presence of an alcoholate at temperatures to 60° C. The reaction product is then converted with tosylchloride or mesylchloride into a compound of formula VI, preferably in an inert solvent, for example methylene chloride.

Another method of preparing the compounds of formula I wherein R contains nitrogen or oxygen consists of a reaction of a compound of formula VII

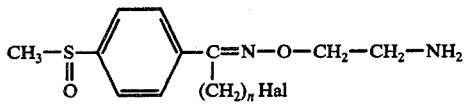

with a compound of formula VIII M$^1$—R$^1$ in which formulae n has the value 4 or 5, Hal is a halogen atom preferably a chlorine or bromine atom, M' is an alkali metal atom and R' is a cyano group or a methoxy group or an ethoxy group.

This reaction is preferably carried out in an inert solvent, for example ethanol, dimethyl sulfoxide, dimethyl formamide and the like at temperatures between 0° and 70° C.

The compounds of formula I wherein R contains an oxygen atom can also be obtained by converting a compound of formula IX

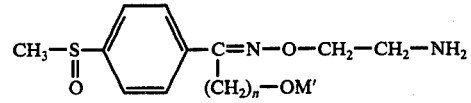

with a compound of formula X R—R''. In this formulae M' is an alkali metal atom, R$_3$ is a halogen atom, for example a chlorine atom or a bromine atom, or a group (SO$_4$) ½, R'' is a methyl or ethyl group, and n has the value 4 or 5.

The reaction is preferably carried out in an inert solvent, for example toluene or dimethyl formamide. As a rule the reaction takes place at a temperature between 0° and 80° C.

The compounds of formula I can also be obtained by hydrolyzing a compound of formula XI

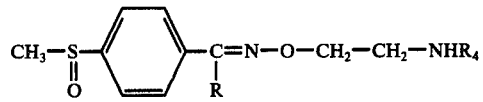

wherein R$_4$ is a protective group, for example, a trityl group. The reaction can be carried out in a water-mixed inert solvent, in acid conditions, at a temperature between room temperature and 100° C.

The compounds can also be obtained by oxidizing a compound of formula XII

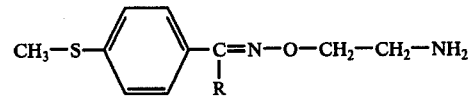

or a salt thereof. As an oxidation agent may be used, for example, peracids, for example m-chloro-perbenzoic acid. The bromine complex of 1,4-diazabicyclo [2.2.2.] octane may also be used. As solvents may be used methylene chloride, dilute acetic acid and the like. As a rule the reaction temperature is between 0° and 50° C.

The invention will be described in greater detail with reference to the following specific examples.

1. 4'-Methylsulphinylvalerophenone 0-(2-aminoethyl) oxime fumarate (1:1)

22.5 Mmol (5.0 g) of 4'-methylsulphinylvalerophenone (melting point 80–82° C), 22.5 mmol (3.3 g) of 2-aminooxyethylamine dihydrochloride and 3.6 ml of pyridine were refluxed for 2 hours in 30 ml of absolute ethanol. After evaporating the pyridine and the ethanol in vacuo, the residue was dissolved in water. This solution was washed with petroleum ether and 45 ml of 2N sodium hydroxide solution were then added. Five extractions with 40 ml of chloroform were then carried out. The extract was washed three times with 20 ml of water. After drying on sodium sulphate it was evaporated in vacuo. Toluene was then evaporated another three times (so as to remove the pyridine). The resulting oil was dissolved in absolute ethanol and an equimolar quantity of fumaric acid was added. Then there was heated until a bright solution was obtained after which there was crystallized at +5° C. After sucking off and washing with cold ethanol there was dried in air. The resulting title compound had a melting point of 133° C.

2. 4'-Methylsulphinylcaprophenone 0-(2-aminoethyl) oxime hydrochloride 75.0 Mmol (17.9 g) of 4'-methylsulphinylcaprophenone (melting point 93–94° C), 75.0 mmol (11.2 g) of 2-aminooxyethylamine dihydrochloride and 15 of pyridine were stirred at room temperature for 3 days together with 75 ml of absolute ethanol. The pyridine and the ethanol were then evaporated in vacuo and the residue was dissolved in water. 100 ml of 2N NaOH were added to this solution and 4 extractions with 50 ml of $CH_2Cl_2$ were carried out. The extract was then dried on $Na_2SO_4$ and evaporated in vacuo. Toluene was evaporated another three times. The residue was dissolved in ethanol and an equimolar quantity of 3N alcoholic hydrochloric acid was added. The ethanol was then removed in vacuo and the residue was crystallized successively from ethanol (1x), acetonitrile (2x) and dioxan (1x). The resulting title compound had a melting point of 125.5°–126.5° C.

3. 4'-Methylsulphinylheptanophenone 0-(2-aminoethyl) oxime fumarate (1:1)

8 Mmol (2.0 g) of 4'-methylsulphinylheptanophenone (melting point 91°–92° C), 8 mmol (1.2 g) of 2-aminooxyethylaminedihydrochloride and 0.8 ml of pyridine were refluxed for 2½ hours in 15 ml of absolute ethanol. After evaporating the pyridine and ethanol in vacuo the residue was dissolved in water. The solution was washed 2 times with 20 ml of ether after which 20 ml of 2N NaOH were added. Three extractions with 60 ml of methylene chloride were then carried out. The extract was washed with 5% sodium bicarbonate solution (2x) and with water (1x), dried on sodium sulphate and evaporated in vacuo. Toluene was then evaporated another three times. The resulting oil was dissolved in absolute ethanol and an equimolar quantity of fumaric acid was added. On heating a clear solution was obtained which crystallized out at +5° C. After filtering under reduced pressure and washing with an ethanol/ether (1:1) solution the product was dried in air. The resulting title compound had a melting point of 109°–112° C.

4. 4'-Methylsulphinyl-2-phenylacetophenone 0-(2-aminoethyl) oxime hydrochloride.

The free base of the title compound was obtained as an oil from 4'-methylsulphinyl-2-phenylacetophenone (melting point 104°–104.5° C) in a manner analogous to the synthesis of example 3. This oil was converted into the hydrochloride salt with ethanolic hydrochloric acid. Crystallization followed, after evaporating the ethanol, from ethanol/ether (1:1). Melting point 158°–159° C.

5. 5-Ethoxy-4'-methylsulphinylvalerophenone 0-(2-aminoethyl) oxime fumarate (1:1)

The title compound was obtained from 5-ethoxy-4'-methylsulphinylvalerophenone (melting point 69°–71° C) in a manner analogous to the synthesis of Example 3. Crystallizations from successive solutions ethanol/ether (1x) and isopropanol (1x) yielded the title compound having a melting point of 93°–96° C.

6. 6-Methoxy-4'-methylsulphinylcaprophenone 0-(2-aminoethyl) oxime

In a manner analogous to Example 3 the title compound was obtained as a resin from 6-methoxy-4'-methylsulphinylcaprophenone (melting point 74°–77° C).

7. 5-Cyano-4'-methysulphinylvalerophenone 0-(2-aminoethyl) oxime fumarate (1:1)

In a manner analogous to Example 3 the title compound having a melting point of 115°–117° C was obtained from 5-cyano-4'-methylsulphinylvalerophenone (melting point 89.5°–91.5° C).

8. 6-Cyano-4'-methylsulphinylcaprophenone 0-(2-aminoethyl) oxime

In a manner analogous to Example 3, the title compound was obtained as a resin from 6-cyano-4'-methylsulphinylcaprophenone (melting point 58.5°–60.5° C).

9. 5-Cyano-4'-methylsulphinylvalerophenone 0-(2-aminoethyl) oxime fumarate (1:1)

8.0 Mmol (4.3 g) of 5-cyano-4'-methylsulphinylvalerophenone 0-(2-tritylaminoethyl) oxime were dissolved in 40 ml of 90% acetic acid. After standing at room temperature for 3 days, this reaction mixture was evaporated to dryness in vacuo and thereafter the residue was dissolved in 80 ml of ether. The resulting solution was extracted with 40 ml of 0.2 N hydrochloric acid and the extract, after rendering alkaline with 10 ml of 2N sodium hydroxide solution, was extracted with successively 50 and 25 ml of methylene chloride. The resulting solution was dried on sodium sulphate and evaporated in vacuo. The residue was dissolved in 70 ml of absolute ethanol after which an equimolar quantity of fumaric acid was added. Crystallization followed at 5° C. Melting point 114°–117° C.

10. 4'-Methylsulphinylcaprophenone 0-(2-aminoethyl) oxime hydrochloride.

8.0 Mmol (2.02 g) of 4'-methylsulphinylcaprophenone oxime (melting point 96°–97° C, 8.2 mmol (0.95 g) of 2-chloroethylamine hydrochloride and 1.11 g of KOH powder were added, while stirring at 20° C, to 10 ml of dimethyl formamide (DMF). After stirring at room temperature for 1 day the DMF was removed in vacuo, the residue was brought in water, after which 2N hydrochloric acid was added until pH=3. The remaining oxime was removed by means of $CH_2Cl_2$, after which 5 ml of 2N sodium hydroxide solution were added. Three extractions with $CH_2Cl_2$ were then carried out. The collected $CH_2Cl_2$ layers were washed with a 5% sodium bicarbonate solution and dried on sodium sulphate. After removing the said $CH_2Cl_2$ in vacuo the residue was processed as described in Example 2. The title compound obtained in this manner had a melting point of 125°–126.5° C.

11. 4'-Methylsulfinylcaprophenone 0-(2-aminoethyl) oxime HCl a. 26 Mmol (1.15 g) of ethylene oxide were led by means of a nitrogen flow while stirring at 55° C into a suspension of 15.5 mmol of 4'-methylsulphinylcaprophenone oxime (melting point 96°–97° C) in 25 ml of absolute ethanol in which 0.03 g of Li had been dissolved. Then stirring was continued for another hour at 60° C. After the addition of 0.3 ml of acetic acid the ethanol was distilled off in vacuo and the residue was purified chromatographically by means of silica gel and with $CH_2Cl_2$ as an eluent. After evaporating the solvent the 0-(2-hydroxyethyl) oxime was obtained as an oil.

b. To a solution of 11 mmol hereof in 70 ml of ethylene chloride, 2.25 ml of triethylamine were added while stirring at $-5°$ to $0°$ C and 12 mmol (0.9 ml) of methylchloride were then added dropwise in approximately 20 minutes. Stirring at $0°$ C was continued for another 30 minutes, the mixture was then successively washed with icewater (4x), a 5% sodium bicarbonate solution of $0°$ C (1x) and a saturated NaCl solution of $0°$ C (2x). After drying on sodium sulphate at $5°$ C, the $CH_2Cl_2$ was distilled off in vacuo at a bath temperature of $40°$ to $60°$ C. In this manner the 0-(2-mesyloxyethyl)oxime was obtained.

c. A mixture of 8 mmol hereof in 30 ml of methanol which contained 245 mmol (4.2 g) of $NH_3$, was kept at $100°$ C in an autoclave for 14 hours. After cooling the methanol was removed in vacuo, the residue was stirred with 50 ml of 2N sodium hydroxide solution and extracted with $CH_2Cl_2$. The collected $CH_2Cl_2$ extracts were washed with a 5% sodium bicarbonate solution. After drying on sodium sulphate and distilling off the $CH_2Cl_2$ in vacuo, the resulting free base was dissolved in ethanol. An equimolar quantity of ethanolic hydrochloric acid was added to the solution. The substance was crystallized from ethanol and from acetonitrile. Melting point $124.5°-126°$ C.

12. 4'-Methylsulphinylvalerophenone 0-(2-aminoethyl) oxime fumarate (1:1)

14 Mmol (3.75 g) of 4'-methylsulphinylvalerophenone ethylene ketal and 14 mmol (2.0 g) of 2-aminooxyethylamine dihydrochloride were refluxed for 4 hours in 20 ml of methanol. The methanol was evaporated in vacuo and the residue was dissolved in water followed by two washings with ether. 3 ml of 50% sodium hydroxide solution were then added and three extractions were carried out with 40 ml of $CH_2Cl_2$. This extract was washed with 5% sodium bicarbonate solution and with water. The solution was then dried on sodium sulphate and the $CH_2Cl_2$ was distilled off in vacuo. The residue was dissolved in ethanol. An equimolar quantity of fumaric acid was added. The title compound crystallized. Melting point $131°-133°$ C.

13. 4'-Methylsulphinyl-2-phenylacetophenone 0-(2-aminoethyl) oxime hydrochloride The title compound was obtained as a free base in an identical manner from 4'-methylsulphinyl-2-phenylacetophenone ethylene ketal. This compound was converted into the hydrochloride as described in Example 2. Melting point $157°-158.5°$ C.

14. 4'-Methylsulphinylheptanophenone 0-(2-aminoethyl)oxime fumarate (1:1)

The title compound having a melting point of $108°-111.5°$ C was obtained in an identical manner from 4'-methylsulphinylheptanophenone ethylene ketal. 15. 6-Methoxy-4'-methylsulphinylcaprophenone 0-(2-aminoethyl) oxime 5 Mmol (1.7 g) of 6-methoxy-4'-methylthiocaprophenone 0-(2-aminoethyl) oxime hydrochloride (melting point $86°-87.5°$ C) were dissolved in 70 ml of water and 20 ml of 2N sodium hydroxide solution were added. Four extractions with 40 ml of $CH_2Cl_2$ were then carried out. After drying on sodium sulphate the extract was evaporated to dryness in vacuo. The resulting oil was dissolved in 15 ml of 70% acetic acid and cooled to $0°$ C. Within 1 hour and while stirring at $0°$ C, 5.2 mmol (1.4 g) of the bromine complex of 1.4 diazabicyclo [2.2.2] octane were added scoop-wise. Stirring at $0°$ C was then continued for another 4 hours. The mixture was poured on icewater. While cooling, 20 ml of 50% sodium hydroxide solution were added, succeeded by extraction with $CH_2Cl_2$. The extract was washed with 5% sodium bicarbonate solution and water. After drying on sodium sulphate the $CH_2Cl_2$ was removed in vacuo. The residue was purified chromatographically over silica gel with ethanol/ammonia (95:5) as an eluent. The solvents were distilled off in vacuo. The title compound was obtained as a resin. Equivalent weight: 340.

16. 6-Cyano-4'-methylsulphinylcaprophenone 0-(2-aminoethyl) oxime

10 Mmol (3.2 g) of 6-chloro-4'-methylsulphinylcaprophenone 0-(2-aminoethyl) oxime were dissolved in 10 ml of dimethyl sulfoxide (DMSO). 25 mmol (1.2 g) of sodium cyanide were then added. The suspension was heated at a temperature of $50°$ to $70°$ C for 5 hours and then cooled to room temperature. It was then diluted with 100 ml of 0.5N sodium hydroxide solution and extracted three times with 40 ml of $CH_2Cl_2$. The extract was washed with water, dried on sodium sulphate and evaporated in vacuo. The residue was purified chromatographically over silica gel with ethanol/ammonia (95:5) as an eluent. After evaporating the solvents the title compound was obtained as a resin. Equivalent weight: 321.

17. 5-Ethoxy-4'-methylsulphinylvalerophenone 0-(2-aminoethyl) oxime fumarate (1:1)

12 Mmol (5.2 g) of 5-chloro-4'-methylsulphinylvalerophenone 0-(2-aminoethyl) oxime fumarate (1:1) (melting point $123°-126°$ C) were added to a solution of 240 mgatt (5.5 g) of sodium in 100 ml of absolute ethanol. The solution was then heated at $70°$ C for 8 hours. It was then neutralized at $0°$ C with alcoholic hydrochloric acid and the sodium chloride was filtered off. The alcohol was distilled off in vacuo and the residue was dissolved in water. 50 Ml of 50% sodium hydroxide solution was added to the solution after which three extractions with $CH_2Cl_2$ were carried out. The extract was washed with 5% sodium bicarbonate solution and with water succeeded by drying on sodium sulphate. The $CH_2Cl_2$ was distilled off in vacuo and the residue was converted as described in example 1 into the fumarate (1:1). After crystallization from isopropanol (2x) the title compound having a melting point of $92°-95°$ C was obtained.

18. Tablet 50 mg of 5-ethoxy-4'-methylsulphinylvalerophenone 0-(2-aminoethyl)oxime fumarate (1:1)

335 mg of lactose
60 mg of potato starch
25 mg of talc
5 mg of magnesium stearate
5 mg of gelatin.

19. Suppository 50 mg of 6-methoxy-4'-methylsulphinylcaprophenone O-(2-aminoethyl)oxime 1500 mg of suppository mass.

20. Injection Liquid 25 g of 5-cyano-4'-methylsulphinylvalerophenone O-(2-aminoethyl)oxime fumarate (1:1)

1.80 g of methyl p-hydroxybenzoate
0.20 g of propyl p-hydroxybenzoate
9.0 g of sodium chloride
4.0 g of poly(oxyethylene)$_{20}$ sorbitanmonooleate
water to 1000 ml.

What is claimed is:

1. An oxime ether compound of the formula

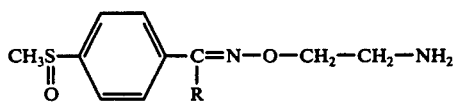

wherein R is a straight chain alkyl group having 4 to 6 C atoms, a benzyl group, a 4-ethoxybutyl group, a 5-methoxypentyl group, a 4-cyanobutyl group or a 5-cyano-pentyl group, and salts thereof with pharmaceutically acceptable acids.

2. The 5-Cyano-4'-methylsulphinylvalerophenone O-(2-aminoethyl) oxime and salts thereof with pharmaceutically acceptable acids of claim 1.

3. The 6-Cyano-4'-methylsulphinylcaprophenone O-(2-aminoethyl) oxime and salts thereof with pharmaceutically acceptable acids of claim 1.

4. An oxime ether compound of the formula:

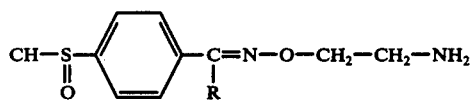

wherein R is a straight chain alkyl of 4 to 6 carbon atoms, benzyl, 4-ethoxybutyl or 5-methoxypentyl and salts thereof with pharmaceutically acceptable acids.

5. The 4'-Methylsulphinylvalerophenone O-(2-aminoethyl) oxime and salts thereof with pharmaceutically acceptable acids of claim 4.

6. The 4'-Methylsulphinylcaprophenone O-(2-aminoethyl) oxime and salts thereof with pharmaceutically acceptable acids of claim 4.

7. The 4'-Methylsulphinylheptanophenone O-(2-aminoethyl) oxime and salts thereof with pharmaceutically acceptable acids of claim 4.

8. The 4'-Methylsulphinyl-2-phenylacetophenone O-(2-aminoethyl) oxime and salts thereof with pharmaceutically acceptable acids of claim 4.

9. The 5-Ethoxy-4'-methylsulphinylvalerophenone O-(2-aminoethyl) oxime and salts thereof with pharmaceptically acceptable acids of claim 4.

10. The 6-Methoxy-4'-methylsulphinylcaprophenone O-(2-aminoethyl) oxime and salts thereof with pharmaceutically acceptable acids of claim 4.

11. A pharmaceutical composition comprising a compound of the formula

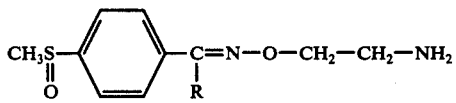

wherein R has the meanings given in claim 1 in an antidepressively effective amount and a pharmaceutically acceptable carrier therefore or a salt thereof with a pharmaceutically acceptable acid.

12. Method of treating patients suffering from depression comprising administering to said patients an antidepressively effective quantity of a compound of the formula:

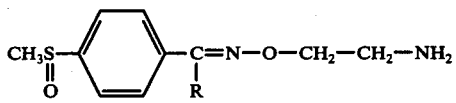

or a salt thereof with a pharmaceutically acceptable acid wherein R has the meaning as in claim 1.

* * * * *